United States Patent
Wist

(10) Patent No.: US 6,243,601 B1
(45) Date of Patent: Jun. 5, 2001

(54) TRANSILLUMINATION IMAGING INSTRUMENTATION WITH SCATTERED LIGHT DISCRIMINATION

(76) Inventor: Abund Ottokar Wist, 9403 Farmington Dr., Richmond, VA (US) 23229

( * ) Notice: Subject to any disclaimer, the term of this patent is extended or adjusted under 35 U.S.C. 154(b) by 0 days.

(21) Appl. No.: 09/156,612

(22) Filed: Sep. 18, 1998

(51) Int. Cl.$^7$ ............................................. A61B 6/00
(52) U.S. Cl. .................... 600/473; 600/476; 600/477; 364/413; 364/414; 364/415; 250/358; 250/360; 250/341; 250/358.1
(58) Field of Search ................... 128/664, 665, 128/653.1; 250/341, 358, 360, 358.1; 600/310, 473, 476, 407, 477; 364/413, 414, 415

(56) References Cited

U.S. PATENT DOCUMENTS

| | | | | |
|---|---|---|---|---|
| 4,515,165 | * | 5/1985 | Carroll | 128/664 |
| 4,807,637 | * | 2/1989 | Bjorkholm | 128/664 |
| 4,829,184 | * | 5/1989 | Nelson et al. | 250/358.1 |
| 4,945,239 | * | 7/1990 | Wist et al. | 250/358.1 |
| 5,371,368 | * | 12/1994 | Alfano et al. | 250/341.1 |
| 5,570,182 | * | 10/1996 | Nathel et al. | 356/345 |
| 5,664,574 | * | 9/1997 | Chance | 128/664 |
| 5,730,133 | * | 3/1998 | Godik | 600/407 |

* cited by examiner

*Primary Examiner*—Marvin M. Lateef
*Assistant Examiner*—Jeoyuh Lin
(74) *Attorney, Agent, or Firm*—McGuireWoods, LLP

(57) ABSTRACT

Transillumination imaging instrumentation is improved by eliminating the detection of stray light beams, and facilitating the detection of light beams which pass straight through an illuminated object. Three dimensional images can be constructed using either curved emitter and detector arrays or by using emitter and detector elements that rotate about a common axis.

9 Claims, 6 Drawing Sheets

TRANSILLUMINATION IMAGING INSTRUMENTATION WITH SCATTERED LIGHT DISCRIMINATION

BACKGROUND OF THE INVENTION

1. Field of the Invention

The invention generally relates to transillumination imaging instrumentation used in the biological setting and, more particularly, to improvements in the design of transillumination imaging devices to prevent scattered light from adversely affecting detection performance, and provide a more useful format for imagery.

2. Description of the Prior Art

Transillumination involves the use of non-ionizing radiation, preferably having wavelengths ranging from 500 nm to 1500 nm, to image an object. Similar to an X-ray, transillumination involves passing radiant energy through an object, and detecting transmitted or reflected radiation. Detection can be accomplished using photocells or other electronic devices, or using photographic film or other image capturing materials. However, particularly when biological imaging is being performed (i.e., breast imaging, teeth imaging, etc.), transillumination offers the advantage of non-ionizing radiation compared to the ionizing radiation used in X-rays which is now widely believed to cause the induction of various cancers. However, one of the drawbacks of using non-ionizing radiation is that it is more easily scattered than ionizing X-rays, thus making it difficult to detect small structures in an object being imaged.

U.S. Pat. No. 4,945,239 to Wist et al., which is herein incorporated by reference, describes several concepts for distinguishing light which passes straight through a sample from light which is scattered from other sources. One method involves using a pair of pin-hole boxes in front of and behind the object being imaged whereby scattered light must traverse straight though spaced apart pin holes in order to reach a detector. Another method involves separately activating an emitter-detector pair, among a plurality of pairs in an array, whereby the timing of activation of the selected emitter-detector pair is used to assure that the light beam passes straight through an object. A variation on this method is to use shutters in front of a detector module whereby the timing of opening the shutter is matched to light emission from a specific emitter. The shutter scheme contemplated in Wist et al. can also be matched to the time of flight of the light through the object. Still another method involves positioning matched polarization filters on either side of an object, whereby scattering events that occur within an object change the plane of polarized light such that it no longer matches the filter positioned in front of a detector and the scattered light is not detected. Phase plates with a plurality of adjacent polarized regions can be used in combination with emitter and detector arrays, thereby eliminating the need for mechanically moving a light source.

In recent years the use of three dimensional modeling or imaging has become a useful and popular tool in many fields including the medical field. This popularity is due in part to the increased ability of computers to receive and process large amounts of raw data required for three dimensional images. Transillumination imaging is useful not only for detection but for providing detailed locations of anomalies in body parts. Using transillumination to form a three dimensional image provides more information than would be possible with a mere two dimensional image. The present invention can be configured in one of several ways to yield the data required by a computer to produce a three dimensional image of a semi opaque object such as a leg, foot, breast, or tooth, and to detect anomalies therein. Furthermore, the present invention drastically reduces the size of the imaging equipment and reduces the time required to make images.

Articles which demonstrate the utility of transillumination in biological and medical applications include: Wist et al., *IEEE Transactions on Medical Imaging*, Vol. 12, No. 4, December, 1993 (pages 751–757); Wist et al., *J Clin. Laser Med. In Surgery*, 11:313–321 (1993); Wist et al., *J. Clin Laser Med. In Surgery*, 12:165–170 (1994); Swineford et al., *Proceedings of Clinical Applications of Modern Imaging Technology II, SPIE*, Vol. 2132, pp.201–207 (1994); Wist, *SPIE* 2628:286–299 (1995); and Wist et al., *SPIE*, 2389-552–563. These articles show the use of transillumination scanning technology in detecting incipient caries in teeth and identifying objects in tissues.

SUMMARY OF THE INVENTION

It is an object of this invention to provide transillumination instrumentation and methods which provide for improved object detection in biological samples, and which are of a compact size.

Another object of this invention is to provide a mechanism for quickly processing sensed transillumination signals over a very large signal range.

Another object of this invention is to provide a method for matching a discriminating plate to a laser and detector array combination.

Another object of this invention is to provide transillumination instrumentation that have specific applications in imaging teeth.

Another object of this invention is to provide methods using transillumination for creating three dimensional images.

Another object of this invention is to provide a method for creating an accurate transillumination image using a single light source.

Another object of this invention is to use the laser speckle effect to produce transillumination images.

According to the invention, an array of diodes is placed on one side of a semi opaque object and the light passing through the object is received by an array of detectors. The diodes may be lit sequentially or coded and lit all at once, the character of light received at each of the detectors is analyzed to determine if abnormalities are present. The light received by the detectors is essentially a cross-sectional image of the examined semi opaque object. Light passing through the semi opaque object may be deflected causing stray light beams which will result in a distorted image of the object or any anomaly found therein or result in missing an anomaly altogether. To improve image quality and detection ability a mechanical discriminator in the form of a substrate is placed in front of the detector array. The mechanical discriminator contains a plurality of optical passages each aligned with detectors behind the substrate. The optical passages allow only perpendicular light beams to traverse the substrate to the detector. Stray light beams are excluded by the walls of the optical passages. The optical passages are 1–100 $\mu$m in diameter and 100–10,000 $\mu$m in length and normally have a diameter to length ratio of 1/100. The optical passage walls may be roughened to further absorb any stray light which might strike the optical passage walls. When light emitted from an array is passed through an object of study and detected on the opposite side by a detector array it is said that one scan has been completed.

In a variation of the invention, a single light source can be used to produce an accurate two dimensional transillumination image by positioning a light discriminator, equipped with optical passages that are not parallel to each other, between a light source and a detector array. A single light source for providing non-collimated light will produce a fan type beam of light. Optical passages are provided in the mechanical discriminator that will allow only light radially emitted from the light source to pass through and strike the detector array. When a semi opaque object is placed between the light source and the detector array, set at a predetermined distance apart, some light passing through the object will be deflected causing stray light, however; only light traveling radially outward from the light source straight through the object will traverse the discriminator via an optical passage. This configuration is easily set up and less costly than others; however, a predetermined distance must be maintained between the light source and the discriminator and detector. This configuration is particularly well suited for imaging teeth because the light source can be placed outside the mouth thereby alleviating any size constraints. The light source can be for example, a mercury light, a light emitting diode, or any source which produces a suitable light.

In another variation on the invention, alternating emitter-detector arrays are used. Until now, emitter and detector arrays have been grouped primarily with the emitter array on one side of the subject object and the detector array on the other, however arrays containing alternating emitter and detector elements placed on either side of the subject object forming alternating emitter-detector pairs can provide many advantages. One such advantage is that two images may be formed simultaneously. Comparing these two images together will enhance the accuracy of the transillumination imaging process, as well as detection ability. To maintain appropriate positioning the emitter sources and detectors can be mechanically connected. Another advantage is that not only will collimated light be detected and recorded but also reflected light can be detected and analyzed.

Alternating emitter-detector pairs are particularly useful in producing three dimensional images. By using alternating emitter detector pairs in conjunction with an array geometry where the emitter-detector pairs are not parallel or an array configuration that encompasses the target object (e.g., a curved or semicircular array), a complete two dimensional image can be made of the target object as well as pin point the location of any anomalies within the scanned plane. To obtain the data needed to form a three dimensional image a cross-sectional image is scanned and stored in a computer database then the transillumination equipment is moved in vertical relation to the cross-section where another cross-sectional image is scanned and stored and so forth. The stored two dimensional cross-sectional images are analyzed and processed using a suitable computer and combined together to form a three dimensional image. To ensure that the cross-sectional views are correctly combined a metal pin can be added to the subject object for reference.

Another method for producing a three dimensional image is to configure a planar emitter array on one side of a target object and a planar detector array on the other, then rotate the arrays through a desired angle about the subject object in increments, scanning the object and storing the image at each increment. After each successive rotation and scan the scanned image is stored in a database and the next scan is taken. Each scan is retrieved from the image database and processed and combined with the preceding image to produce a three dimensional image. A metal pin may be added to the subject tissue before scanning is started as a referencing aid to be used when combining the individual scans. It should be noted that while not interchangeable, either a mechanical discriminator or coded light can be used to prevent the detection of stray light in either of the above-mentioned methods. It should also be noted that a mechanical device can be used to translate the transilluminatig equipment; however, if arrays of adequate size are used then mechanical translation will not be necessary.

A third method for obtaining three dimensional images from transillumination equipment involves the use of simple thickness contours. As a simple light beam penetrates an object, a detector array placed opposite the light emitter measures the light attenuation. From the measured light attenuation an approximation of depth can be made. A scan conducted in this manner will result in a thickness contour of the subject object. A subsequent second scan of the object rotated 90 degrees will result in a second thickness contour. By referencing these two thicknesses together a rough three dimensional image can be formed. When scanned from all sides a complete three dimensional image can be formed. It will be determined by the size of the specimen to be scanned whether or not a mechanical mechanism is the more practical method available to make a full scan. Images produced in three dimensions via computer require a frame of reference and positional data. A computer analyzes supplied spacial data with respect to a predetermined frame of reference and makes a best fit estimation where data is insufficient. Based upon best fit estimation an image is generated in three space. While this method does have some degree of error it is more that sufficient for determining the size and location of an anomaly inside a breast, tooth or sample of biological tissue.

A fourth method for producing an image uses a phenomena known in the art as laser speckle. Laser speckles are inherent in any laser image and for most practical purposes are not removable. Lasers use coherent light and since most surfaces posses imperfections and slight differences exist for each ray traveling through a medium, interferences will occur between adjacent rays thus reducing or enhancing detected intensities. Laser speckle is especially prevalent when laser light is detected after passing through an object and subsequently produces different patterns when passed through different mediums. Therefore, the present invention proposes to use the laser speckle phenomena to detect the presence of carcinomas and the like within examined tissue by analyzing the differences in laser speckle patterns after passing through a tissue specimen.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
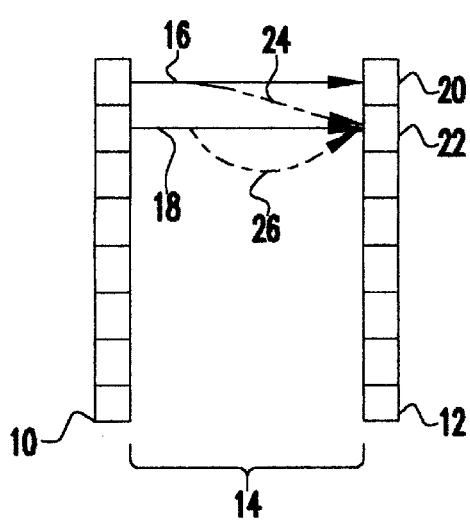
FIG. 1 is a schematic side view of a plurality of light emitters and a plurality of light detectors illustrating discrimination between two adjacent light paths, but no discrimination for stray light from a light source between a matched light source and detector pair.

FIG. 1 shows an emitter array 10 spaced away from a detector array 12. Space 14 accommodates an item to be imaged. This invention is primarily directed to biological and medical applications, therefore the arrays 10 and 12 would be positioned to image, for example, a body part or tissue such as a tooth or breast. The emitter array 10 produces a plurality of collimated light beams 16 and 18 which are directed towards specific detectors 20 and 22. Stray light 24 from light beam 16 may be deflected from its intended path towards detector 22 upon encountering an object inside the item being imaged. If this stray light were not discriminated against at detector 22, an object in the path of light beam 18 may not be detected.

As discussed in detail in U.S. Pat. No. 4,945,239 to Wist et al., there are several techniques which can be used to discriminate against stray light beam 24 at detector 22. For example, light 16 could be polarized or have an embedded signal (e.g., pulse code, etc.), and array 12 could include a polarization plate or signal detection circuitry at detector 22 which would only sense light 18, and would discriminate out stray light 24. Also, array 12 could have a shutter mechanism associated with detectors 20 and 22 that considers only the time of flight of light pulses for light beams 16 and 18. It is envisioned that the instrumentation of this invention will have a discrimination means such as those discussed above, those presented in U.S. Pat. No. 4,945,239, or comparable equipment which will function to eliminate stray light 24 from being detected by detector 22.

Of particular concern in the present invention are the instances when stray light 26 is deflected by an object in the item being imaged, and then is deflected one or more times such that it is directed back towards detector 22. In these instances, the phase plate or embedded signals methodology described above will not effectively discriminate against stray light 26. Thus, objects in the path of beam 18 will be difficult to detect. While the time of flight discrimination methodologies and light shuttering methodologies described in U.S. Pat. No. 4,945,239 to Wist et al. may allow discriminating against stray light 26, these methodologies are expensive, can be unreliable, and can occupy a great deal of physical space which would make imaging small objects impossible. Likewise, the pin-hole box methodology described in U.S. Pat. No. 4,945,239 to Wist et al., may provide a low cost mechanism for capturing stray light of all kinds, this technique is very bulky and not practical for use in many applications. Thus, this invention specifically contemplates using a compact, simple and effective means for discriminating against stray light problems such as that shown in FIG. 1.

Figure 2:
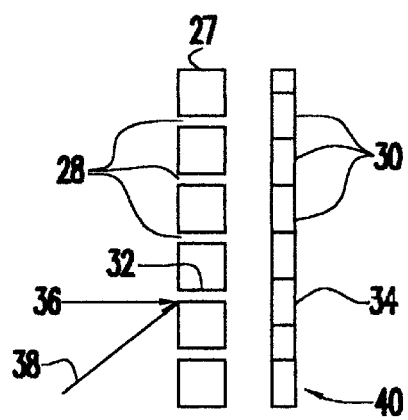
FIG. 2 is a schematic view of a mechanical light discriminator for stray light from a light source between a matched light source and detector pair.

With reference to FIG. 2, a mechanical discriminator 27 is positioned in front of a detector array 40. The mechanical discriminator 27 includes a plurality of optical passages 28, and these passages are aligned with sensors 30. For exemplary purposes, the bottom portion of the mechanical discriminator 27 shows passage 32 aligned with sensor 34. The passage is of length and diameter dimensions that assure that light 36 passing straight through an object of interest will also pass straight through the passage 32 and be detected by detector 34; however, scattered and stray light 38 will not pass through the passage 32 (e.g., it will impact on opaque portions of mechanical discriminator adjacent passage 32 or will impact on the side walls of passage 32). It is recommended that the passage 32 be on the order of 1–100 $\mu$m in diameter, and 100–10,000 $\mu$m long. Most preferably the diameter will range from 10 $\mu$m to 50 $\mu$m, and the length will range from 1,000 $\mu$m to 2,000 $\mu$m, and that the ratio of diameter to length will be greater than 1/10 and will approach 1/100 or more. Experiments have been conducted which demonstrate a 1/100 ratio will result in $10^4$ attenuation of scattered light. The company Collimated Holes Inc. produces plates with micro holes having a diameter of 20 $\mu$m and length of 2 mm, and these plates may be useful in the present invention.

Preferably, the mechanical discriminator 26 will be positioned directly adjacent the sensor array 40 to make a very compact unit. In addition, in some applications, it may be advantageous to integrate the mechanical discriminator 26 with the sensor array 40.

Figures 3A, 3B:
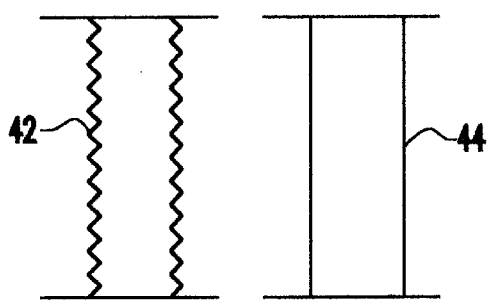
FIGS. 3a and 3b are enlarged cross-sectional side views of alternative openings in a mechanical light discriminator.

FIGS. 3a and 3b show alternative examples of the sidewalls of a passage in a mechanical discriminator according to this invention. The sidewalls 42 shown in FIG. 3a are roughened slightly, as can be achieved using chemical etch or other procedures, while the sidewalls 44 shown in FIG. 3b are smooth. The roughened sidewalls 42 are preferred since they will cause stray light to be reflected, dispersed, or absorbed in such a manner that it will not be successful in traversing the entire length of the passage. By contrast, smooth sidewalls 44 can result in stray light being reflected off of opposing portions of the passage, in a manner akin to light travel in a fiber optic, thereby permitting the stray light to traverse the entire passage. However, in certain applications, smooth walls 44 may be preferred to roughened sidewalls 42.

Figure 4:
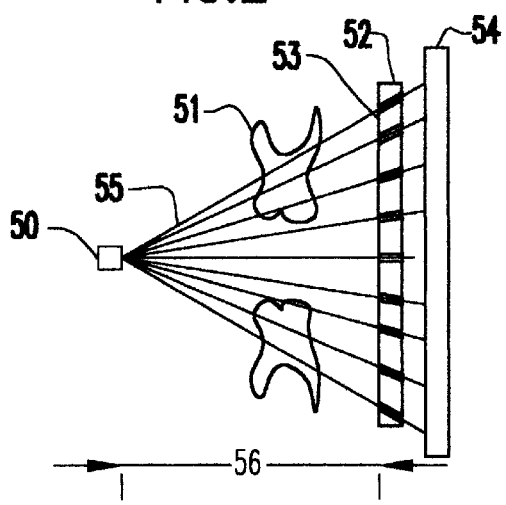
FIG. 4 is a schematic side view of a single light source and detector array.

FIG. 4 shows a non-collimating light source 50 emitting a light beam 55 that passes through a semi opaque object 51, a mechanical discriminator 52 having optical passage 53 which allows light at predetermined angles to traverse the mechanical discriminator 52 and strike the detector array 54. The non-collimating light source 50 emits a wide angle light beam 55, and is maintained at a predetermined distance 56 from the mechanical discriminator 52. The discriminator 52 contains a plurality of optical passages 53 which are radially aligned with the wide angle light beam 55 for predetermined distance 56. The distance 56 may not be varied for a particular configuration else the optical passages will incorrectly discriminate the light directed toward the detector array 54; however, it should be noted that the light source 50 may be initially set up at any desired distance 56. This configuration is particularly useful for dental applications such as cavity detection where space is limited. The light 50 may be positioned outside the mouth, while the detector array 54 and discriminator 52 may be positioned inside the mouth on the opposite side of the targeted semi opaque object, which in this example is teeth 51. In a preferred embodiment of FIG. 4 the light source 50 may be connected to the detector array 54 by some mechanical means such as a bracket (not shown) and the distance between the detector 54 and the source 50 may be adjusted using a light meter before being inserted into a patient's mouth. The embodiment in FIG. 4 is not limited to one light source. For example, if the scanned area is enlarged, another light source can be added, and more optical passages added for the new light source in the same manner. Other light source types such as diode light sources (which have a natural spread) or lasers fitted with appropriate filters can also be used in the FIG. 4 configuration. Additionally, using light sources of different colors may provide advantages in some applications.

Figure 4A:
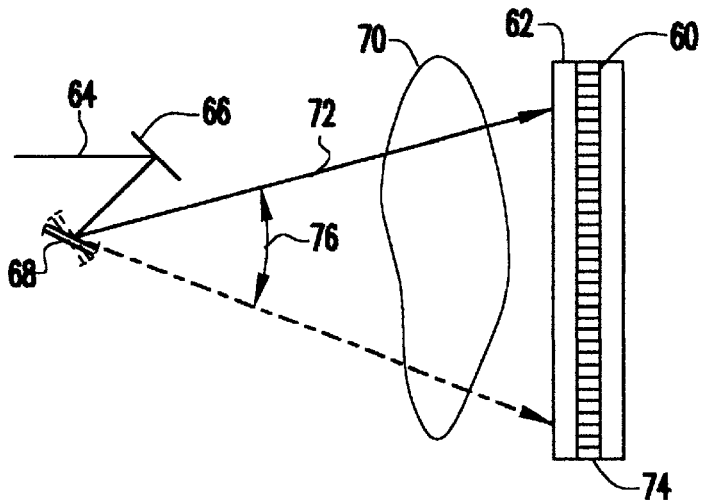
FIG. 4A is a schematic side view of a single collimated light source, mirror configuration, and detector array.

FIG. 4A shows a detector array 60 fitted with a discriminator plate 62 in the same manner as FIG. 4. In FIG. 4A the light source is a single collimated light 64 which is directed via a stationary mirror 66 to a mirror 68 mounted on a galvanometer. An object 70 is scanned by translating the light beam 72 through some angle 76. The light beam is translated by the mirror 68 mounted on the galvanometer. Optimally, this embodiment includes a micro channel plate 74 which increases light sensitivity.

The micro channel plate consists of 10,000 to 1,000,000 very thin tubes that can electronically amplify incoming light by factors of up to 1000. However, some disadvantages of incorporating this into the design include the need for a power supply, complexity, and cost. It should be obvious that micro channel plates can be used with many of the transillumination embodiments described in this application. Alternately, micro channel plates can be used to amplify the detectable light passing through an illuminated object and allow the amplified light to impinge on photosensitive material thereby creating an image.

Figure 5:
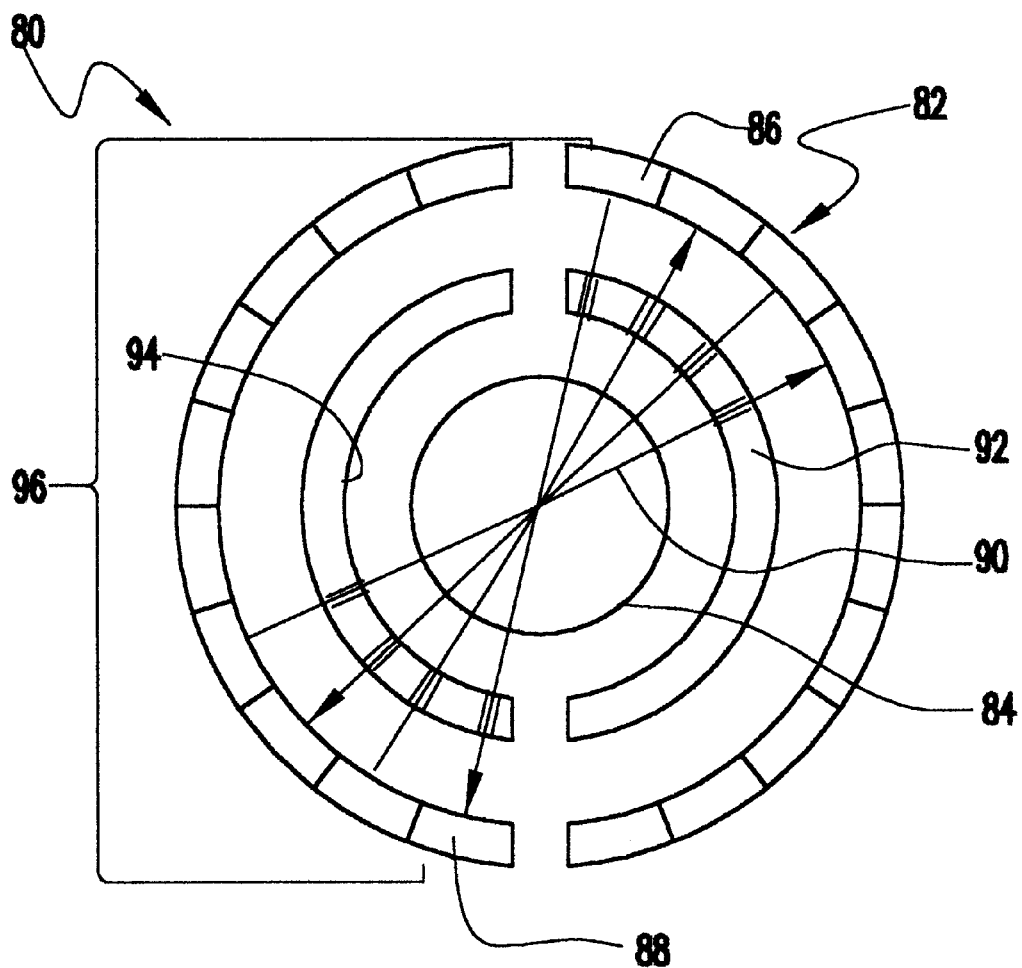
FIG. 5 is a schematic top view of alternating emitter/detector arrays in a semi circular configuration;.

FIG. 5 shows an embodiment of the invention using two complementary alternating emitter-detector arrays 80 and 82 on opposite sides of a semi opaque object 84, where both emitter-detector arrays are semicircular. A plurality of emitter/detector pairs are formed by complementary emitter-detector arrays 80 and 82, where an emitter/detector pair 96 comprises emitter element 86 and detector element 88. A light beam 90 is emitted from emitter element 86 on array 82 and collimated as it passes through the discriminator 92, then said light beam 90 passes through semi opaque object 84 and discriminator 94 before striking detector 96 on array 80. Each array 80 and 82 produces an image of the target object from an opposite side thus, two images are produced in one scan. Using complementary emitter-detector arrays 80 and 82 which curve around the semi opaque object 84, 60, three dimensional image data of the object can be easily obtained by alternatively scanning, storing and translating the two arrays 80 and 82 vertically with respect to the plane previously scanned. After the required scanning is completed the data obtained can be analyzed by computer to produce an image.

Figure 6:
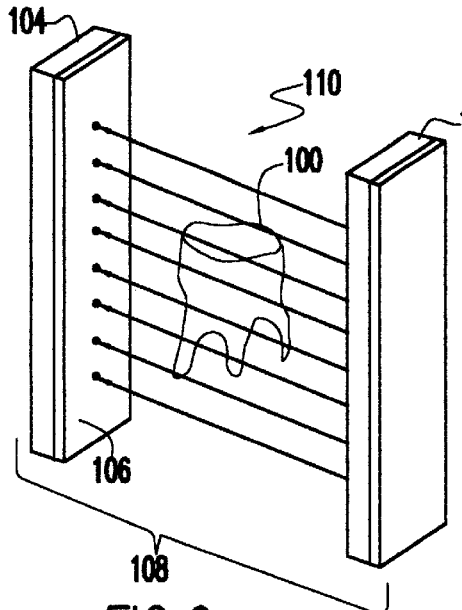
FIG. 6 is an isometric view of emitter and detector arrays positioned to make a single scan of a tooth.

FIG. 6 shows an application of the invention as shown in FIG. 1 and FIG. 2 for producing three dimensional images. A semi opaque object, in this case a tooth 100, is placed between the emitter array 102 and the detector array 104 equipped with mechanical discriminator 106 which allows only light passing straight through the object to strike the detector array 104. After each scan is stored to a computer data base, the transilluminating assembly 108 is rotated, as indicated by arc 110, by a predetermined increment and another scan is taken and stored. Once the transilluminating assembly 108 is rotated through a desired angle of at least 120 degrees the scans are terminated, and all stored scans are retrieved and analyzed by a suitable computer (not shown) to produce a three dimensional image.

Figure 7:
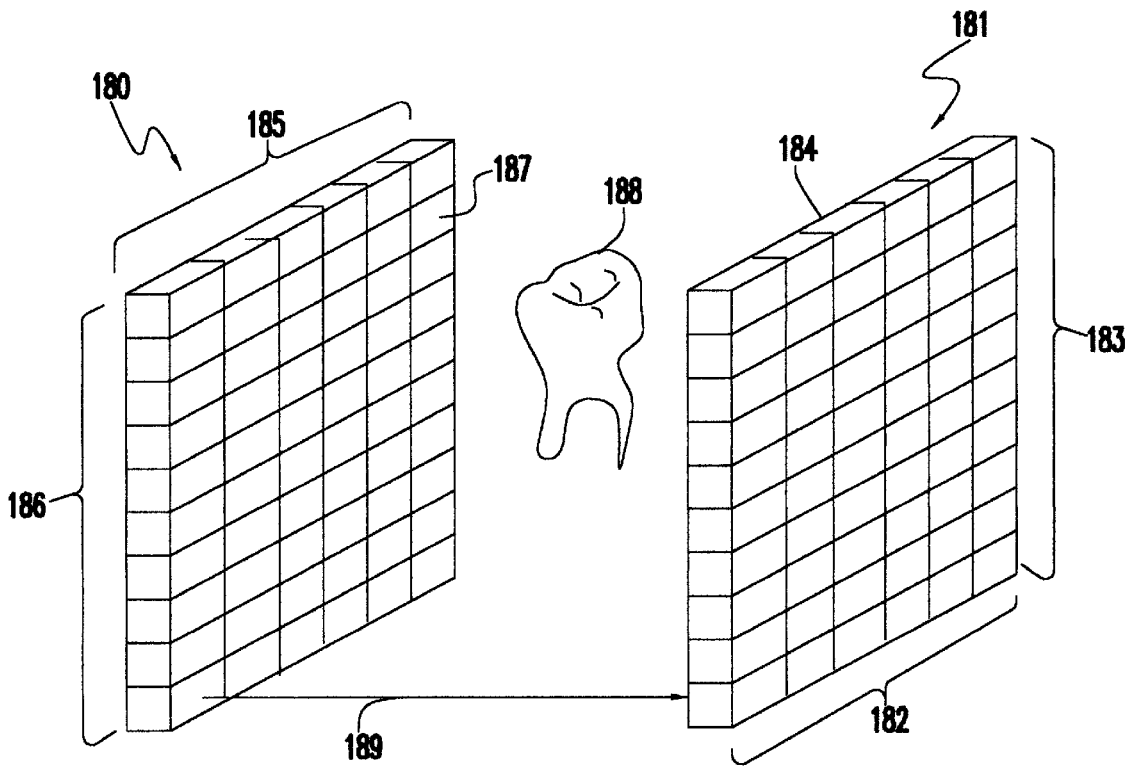
FIG. 7 is an isometric view of and emitter and detector array.

FIG. 7 shows an emitter array 180 which has a plurality of columns 186 and rows 185 of emitters 187, and a detector array 181 which has corresponding rows 182 and columns 183 of detectors 184. Tooth 188 can be imaged in several different manners. For example the emitters 187 on array 180 may be lit by rows 185 from top to bottom successively whereby array 181 is set to receive the emitted light 189 by enabling only those rows 182 of detectors 184 that correspond to the lit emitter rows 185. It should be readily apparent that imaging may be conducted using columns in the same manner. Also, imaging can be conducted by energizing corresponding pairs of emitters and detectors (emitter/detector pairs) in a desired pattern.

If preferred the emitters 187 on array 180 may be lit all at once and received by detector array 181 to produce an image; however, there may be disadvantages to this method. Alternatively, in this instance, using coded pairs of emitters and detectors can help reduce the detection of unwanted stray light. For example, an emitter can be configured to emit coded light and a corresponding detector can be configured to detect only that light which has a the specified code, thus forming a coded emitter/detector pair. Complementary emitter and detector arrays can be setup so that a plurality of differently coded emitter/detector pairs are used.

Using the coded emitter/detector pair method described above each emitter 187 would be distinctly coded and each detector 184 would be set to receive only that light which contains the code from the source emitter 187 to which the detector 184 corresponds.

The emitter array 180 and detector array 181 are shown as planar; however, the geometry of the arrays can be altered to suit any imaging need, for example both arrays may be curved inward to form semicircles as in FIG. 5.

Figure 8:
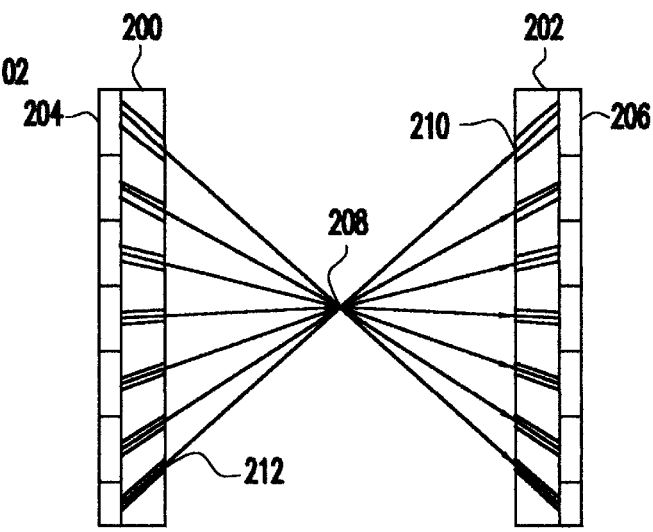
FIG. 8 is a schematic side view of a emitter array fitted with a mechanical discriminator and a detector array fitted with a mechanical discriminator.

FIG. 8 shows yet another emitter/detector array configuration. Similar to FIG. 4 this configuration uses a discriminator plate 202 placed in front of the detector array 206. Each optical passage 210 discriminates against light based on the angle of the light received so that only light at a given angle with traverse the discriminator 202 and strike the detector array. However, in this embodiment an emitter array is used to provide light source for imaging. Specifically, emitter array 204 fitted with discriminator 200 allows only light at predetermined angles to pass and illuminate the object to be imaged. The detectors on array 206 receive only that light from emitter array 204 that is given the same corresponding angle. For example, optical passage 212 allows only light with a predetermined angle to traverse the discriminator. Conversely, optical passage 210 has the same alternate interior angle as optical passage 212 so that light from optical passage 212 can traverse the discriminator 202 on the detector array 206 an be detected.

In this embodiment the emitted light has a convergence point 208 substantially centered between the detector and emitter arrays. Any object to be imaged should be placed so that the object's center is at the convergence point 208. Using this unique configuration an image scan results in a three dimensional image with out rotating the emitter and detector arrays. This configuration is particularly useful for scanning small objects.

Figure 8A:
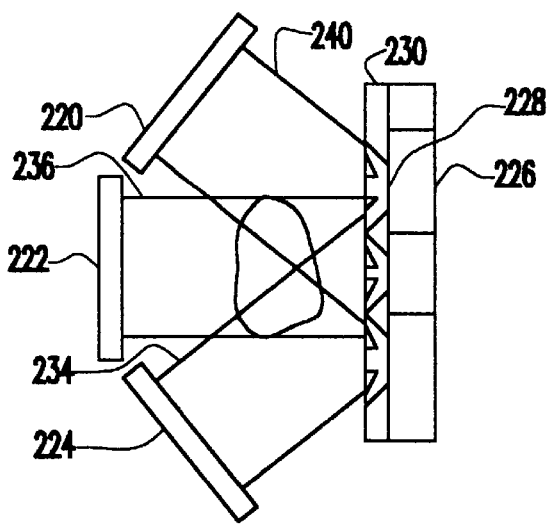
FIG. 8a is a schematic top view of a detector array fitted with a mechanical discriminator and an emitter array arrangement.

FIG. 8A shows another method for imaging an object 232 such as a tooth using detector array 226 having a hole plate 230 wherein holes 228 corresponding to a detector 226 allow light 234, 236, 240 from differing angles to impinge on a detector 226. The holes 228 are angled so as to align with strategically placed emitter arrays 220, 222, 224. The emitter arrays 220, 222, 224 are placed to illuminate the object 232 from different angles thus the detected light 234, 236, 240 produce images from different angles, giving more positional information concerning the object 232 and any characteristics therein.

Figure 9:
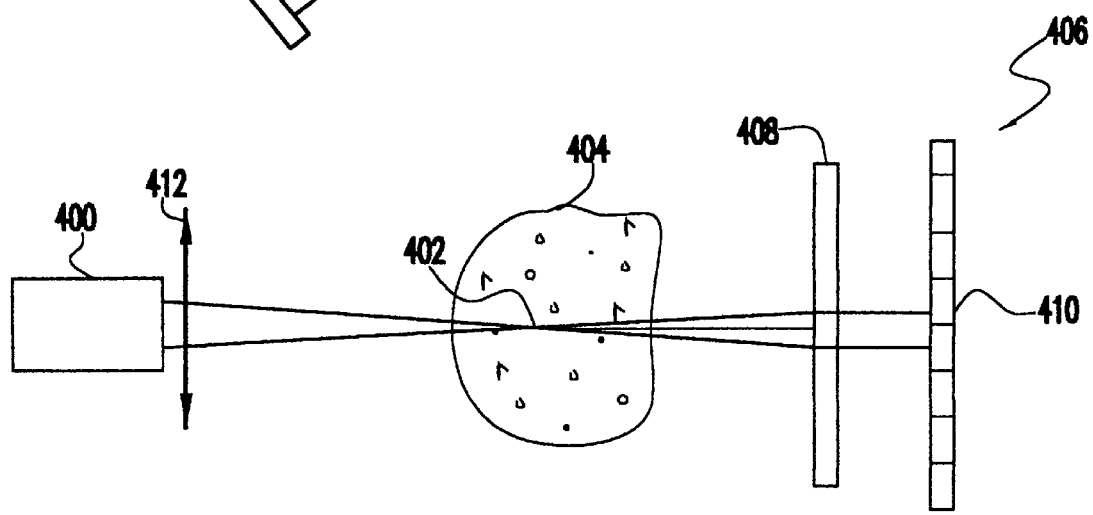
FIG. 9 is a schematic side view of an emitter/detector array fitted with a diffractive plate for scanning using a light beam focused inside a semi-opaque object.

FIG. 9 shows a diode laser 400 which focuses the emitted light beam at some distance outside the laser body 402. Most lasers devices are capable of being focused some distance from the laser device housing using a series of lenses.

The advantage of using a laser device configured to focus a beam outside the laser housing is that the beam can be focused inside a semi opaque object 404 so that the outside portion would not be exposed to intense laser light which can cause damage. FIG. 9 shows a diode laser setup wherein the laser beam focuses 402 inside the semi opaque object 404 and diverges thereafter. The detector array 406 is placed behind a diffractive plate 408 so that the diverging beam is made perpendicular to the plate 408 as it passes through. The altered beam strikes detector 410 and is detected. The laser 400 can be translated along the path indicated by the arrows 412 so that the semi opaque object 404 can be fully scanned. Also, multiple lasers can be used so that translation of a single laser is not necessary to scan an object.

Figure 10:
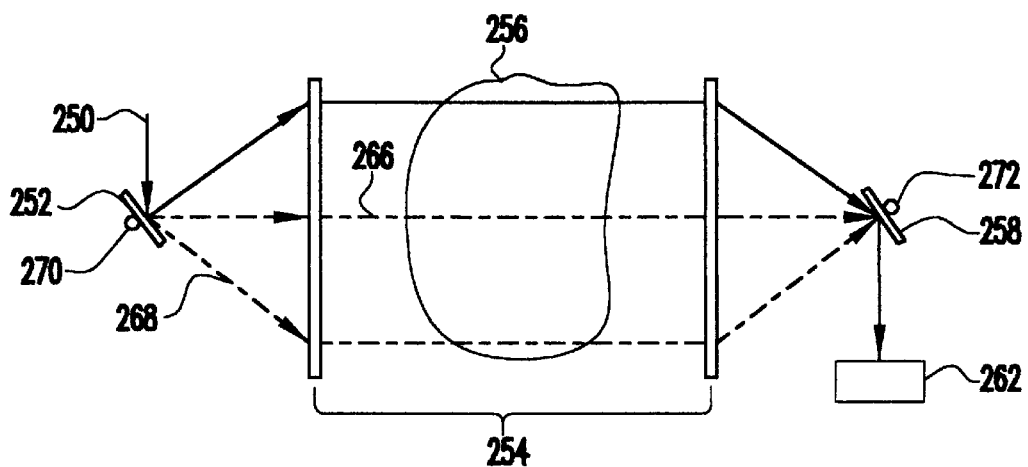
FIG. 10 is a schematic side view of a single collimated light source, with mirrors for reflecting the light beam towards a diffractive plate which causes the light passing through to be perpendicular to the plate and a second diffractive plate for directing the light towards a mirror where the mirror reflects light towards a light detector.

FIG. 10 uses a collimated light source (not shown) which emits light beam 250 which is reflected by mirror 252 mounted on a galvanometer 270 through a diffractive plate 254. The diffractive plate 254 directs the light beam 250 so that the beam is perpendicular to the plate and subsequently passes straight through the object 256. Once the light beam passes through the object 256 a second diffractive plate directs the light beam towards a mirror 258 mounted on a second galvanometer 272 which in turn directs the light beam to a detector 262. Subsequent scans (denoted by the hidden lines 266, 268) are made by adjusting the mirrors 252 and 258 until the object 256 is completely scanned. All light beams passing between the diffractive plates 254 and 255 are substantially parallel to each other. Positional information from the first galvanometer 270, the second galvanometer 272, and data from the detector 262 is collected and stored in a computer (not shown) which will reconstruct an image from the stored data. For each scan the mirrors 252 and 258 are adjusted then readjusted for the next scan. In this manner each scan can be thought of as an image pixel. Using this scanning method laser speckle can be recorded from the detector 262 and later analyzed for pattern changes which can indicate internal differences (e.g. lesions or carcinomas) in object 256. Laser speckle methods can be applied to all laser applications of transillumination.

Figure 11:
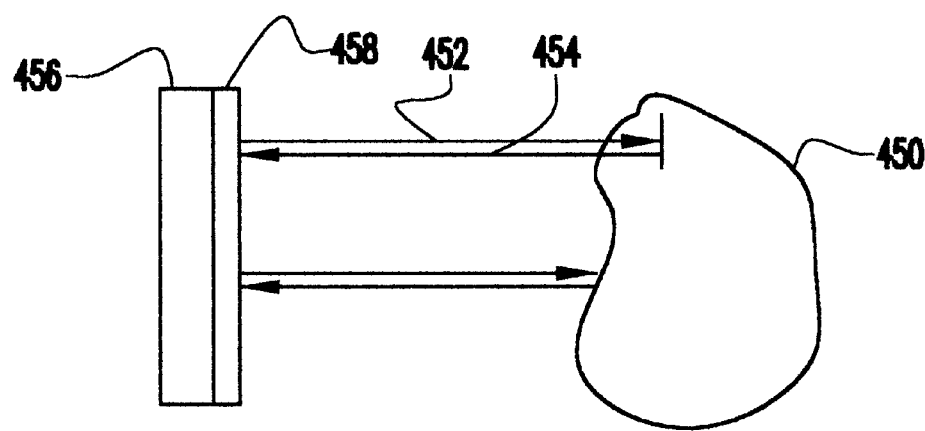
FIG. 11 is a schematic side view of an emitter/detector array fitted with mechanical discriminator.

FIG. 11 shows an image producing setup that utilizes only reflected light to produce the image. This setup requires a emitter/detector array 456 and a hole plate discriminator 458 so that only light perpendicular to the discriminator plate is emitted 452 and only reflected light 454 perpendicular to the discriminator plate is detected.

When light strikes a photo detector cell in a detector array the photo detector cell produces a voltage proportional to the intensity of the light so that the signal produced is analog. Because the signal is analog it needs to be converted to a digital signal before being introduced to a computer for storage and analysis. Because of the large data output from the detector arrays a conventional high speed analog to digital converter is inadequate.

Furthermore, the number of levels needed are in the range of $10^9$ which is more than most computers can handle. Therefore, the schematic diagram in FIG. 12 has been devised.

Figure 12:
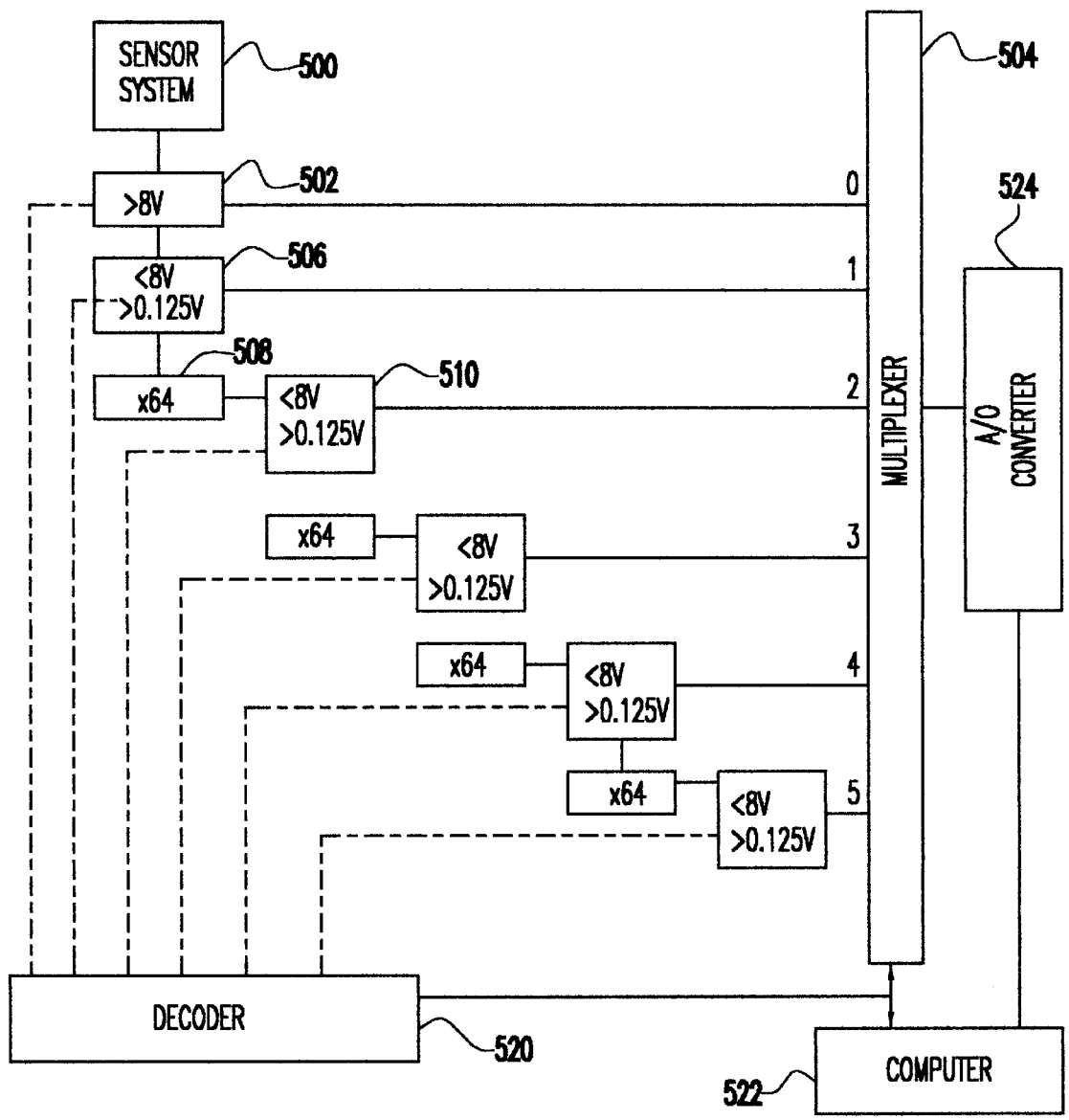
FIG. 12 is a functional block diagram for an interface between a multiplexer, decoder, analog to digital converter, and computer.

FIG. 12 shows a schematic diagram for extending the capabilities of an analog to digital converter to the levels needed. A signal from the sensor system 500 is tested to determine is it is above 8 volts 502. If yes then it is put in channel 0 in multiplexer 504. If not the signal is tested for voltages between 8 volts and 0.125 volts 506. If yes then the signal is put in channel 1 in multiplexer 504. If no the signal is multipied by 64 508 and tested for voltages between 8v and 0.125v 510. If yes then the signal is put in channel 2 multiplexer 504 and so on until the signal is categorized into a channel.

The decoder 520 receives a signal from the multiplexer which tell the multiplexer 504 and computer 522 which channel is active. The multiplexer opens the indicated channel so that the A/D converter 524 converts the signal and sends it to the computer 522 which can address the signal according to its channel and subsequently determine if the signal is shifted (multiplied).

Figure 13:
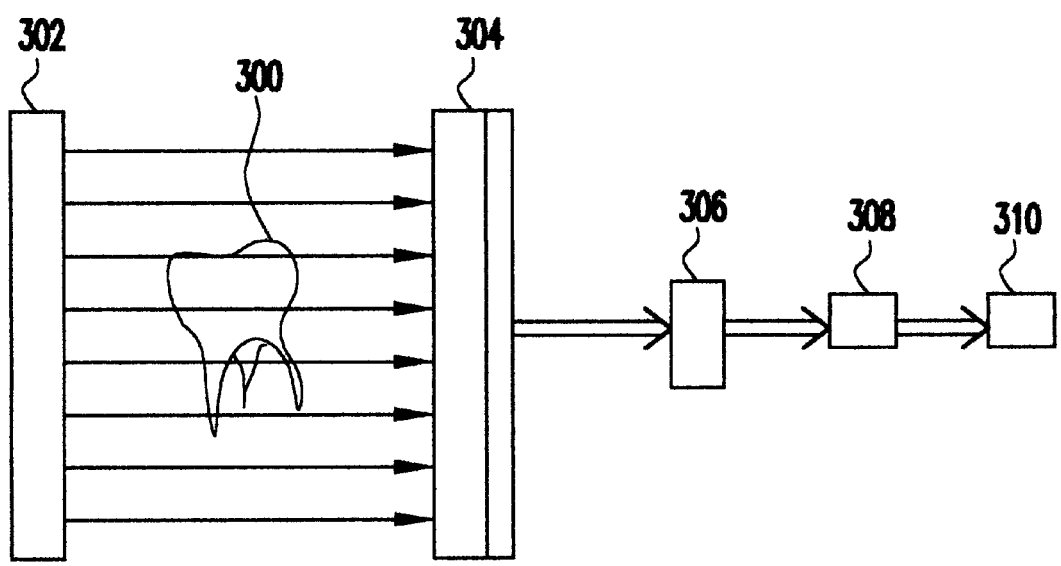
FIG. 13 is a schematic diagram of a typical transillumination setup.

FIG. 13 shows a typical transillumination setup whereby the object 300 is scanned using a light source 302 and a detector array 304. Data from the detector array 304 is converted to digital signal 306 and stored in a computer 308 along with positional data from the transillumination equipment. The computer uses the stored information to reconstruct an image of the illuminated object 300 which is displayed on a monitor 310. An example of data sent to the computer would be signals from the detector array 304 indicating the intensity of light detected and positional information indicating the attitude of the transillumination equipment in relation to the initial or previous scan.

All of the transillumination methods described thus far can be configured in a manner similar to FIG. 13.

While the invention has been described in terms of its preferred embodiments, those skilled in the art will recognize that the invention can be practiced with modification within the spirit and scope of the appended claims.

I claim:

1. Transillumination instrument comprising:
   a source of non-ionizing radiation;
   an object imaging section in which objects to be imaged are positioned;
   a detector for receiving said non-ionizing radiation after it has traversed through an object in said object imaging section; and
   a mechanical discriminator positioned adjacent to said detector and spaced away from said source by said object imaging section, said mechanical discriminator comprising at least one passage through which non-ionizing radiation which passes strait through an object in said object imaging section can traverse and be detected by said detector, but which prevents stray radiation which does not pass straight through said object from traversing the passage in the mechanical discriminator comprising a first opening and a second opening, the first and second openings connected by light-absorbing walls defining the passage from the first opening to the second opening, and wherein said passage has a ratio of diameter to length of 1/10 or less.

2. Transillumination instrument comprising:

a source of non-ionizing radiation;

an object imaging section in which objects to be imaged are positioned;

a detector for receiving said non-ionizing radiation after it has traversed through an object in said object imaging section; and a mechanical discriminator positioned adjacent to said detector and spaced away from said source by said object imaging section, said mechanical discriminator comprising at least one passage through which non-ionizing radiation which passes strait through an object in said object imaging section can traverse and be detected by said detector, but which prevents stray radiation which does not pass straight through said object from traversing the passage in the mechanical discriminator comprising a first opening and a second opening, the first and second openings connected by light-absorbing walls defining the passage from the first opening to the second opening, and wherein said passage comprises roughened sidewalls.

3. Transillumination instrument comprising:

a source of non-ionizing radiation;

an object imaging section in which objects to be imaged are positioned;

a detector for receiving said non-ionizing radiation after it has traversed through an object in said object imaging section; and a mechanical discriminator positioned adjacent to said detector and spaced away from said source by said object imaging section, said mechanical discriminator comprising at least one passage through which non-ionizing radiation which passes strait through an object in said object imaging section can traverse and be detected by said detector, but which prevents stray radiation which does not pass straight through said object from traversing the passage in the mechanical discriminator comprising a first opening and a second opening, the first and second openings connected by light-absorbing walls defining the passage from the first opening to the second opening, and wherein said passage comprises smooth sidewalls.

4. Transillumination instrument comprising:

a source of non-ionizing radiation;

an object imaging section in which objects to be imaged are positioned;

a detector for receiving said non-ionizing radiation after it has traversed through an object in said object imaging section; and a mechanical discriminator positioned adjacent to said detector and spaced away from said source by said object imaging section, said mechanical discriminator comprising at least one passage through which non-ionizing radiation which passes strait through an object in said object imaging section can traverse and be detected by said detector, but which prevents stray radiation which does not pass straight through said object from traversing the passage in the mechanical discriminator comprising a first opening and a second opening, the first and second openings connected by light-absorbing walls defining the passage from the first opening to the second opening, wherein said passage has a ratio of diameter to length of 1/10 or less and, wherein said length of said passage is 1,000 $\mu$m to 2,000 $\mu$m.

5. Transillumination instrument comprising:

a source of non-ionizing radiation;

an object imaging section in which objects to be imaged are positioned;

a detector for receiving said non-ionizing radiation after it has traversed through an object in said object imaging section; and a mechanical discriminator positioned adjacent to said detector and spaced away from said source by said object imaging section, said mechanical discriminator comprising at least one passage through which non-ionizing radiation which passes strait through an object in said object imaging section can traverse and be detected by said detector, but which prevents stray radiation which does not pass straight through said object from traversing the passage in the mechanical discriminator comprising a first opening and a second opening, the first and second openings connected by light-absorbing walls defining the passage from the first opening to the second opening, and wherein said passage has a ration of diameter to length of 1/10 or less and wherein said diameter of said passage is 10 $\mu$m to 50 $\mu$m.

6. A transillumination instrumentation, comprising:

a non planar emitter array which comprises a plurality of emitters that emit non-ionizing radiation;

a non planar detector array which comprises a plurality of detectors that detect non-ionizing radiation, each of said plurality of emitters on said non planar emitter array being aligned with a detector on said non planar detector array and constitute an emitter-detector pair, said non planar emitter array and said non planar detector array encompassing a space therebetween; and a mechanical discriminator positioned adjacent said detector array and spaced away from said source by said object imaging section, said mechanical discriminator comprising at least one passage through which non-ionizing radiation which passes straight through an object in said object imaging section can traverse and be detected by said detector, but which prevents stray radiation which does not pass straight through said object from traversing, each passage in the mechanical discriminator comprising a first opening and a second opening, the first and second openings connected by light absorbing walls defining the passage from the first opening to the second opening.

7. The transillumination instrumentation of claim 6 wherein each of a plurality of emitter-detector pairs has an identical distance between an emitter and a detector of said emitter-detector pair.

8. Transillumination instrument comprising:

a source of non-ionizing radiation;

an object imaging section in which objects to be imaged are positioned;

a detector for receiving said non-ionizing radiation after it has traversed through an object in said object imaging section; and a mechanical discriminator positioned adjacent to said detector and spaced away from said source by said object imaging section, said mechanical discriminator comprising at least one passage through which non-ionizing radiation which passes strait through an object in said object imaging section can traverse and be detected by said detector, but which prevents stray radiation which does not pass straight through said object from traversing the passage in the mechanical discriminator comprising a first opening and a second opening, the first and second openings connected by light-absorbing walls defining the passage from the first opening to the second opening, and wherein said passage has a ratio of diameter to length of approximately 1/100.

9. The transillumination instrumentation of claim 6 wherein said non-ionizing radiation has a wavelength ranging from 500 nm to 1500 nm.

* * * * *